United States Patent [19]

Musser et al.

[11] Patent Number: 4,550,172
[45] Date of Patent: Oct. 29, 1985

[54] NOVEL HETEROCYCLIC COMPOUNDS AS ANTIALLERGIC AGENTS

[75] Inventors: John H. Musser, Malvern; Cesario O. Tio, Coatesville, both of Pa.

[73] Assignee: American Home Products Corporation, New York, N.Y.

[21] Appl. No.: 653,755

[22] Filed: Sep. 21, 1984

[51] Int. Cl.⁴ .................. C07D 277/64; C07D 235/16
[52] U.S. Cl. .................................... 548/180; 548/161; 548/163; 548/171; 548/178; 548/221; 548/222; 548/217; 548/305; 548/467; 548/525; 548/546; 548/547; 546/198; 546/199; 546/202; 546/201; 546/205; 546/206; 546/196; 260/239 A; 260/239 B; 260/239 BF
[58] Field of Search ............... 548/161, 163, 171, 178, 548/180, 221, 222, 217, 305, 467, 525, 546, 547; 546/198, 199, 205, 201, 206, 202, 196; 260/239 A, 239 B, 239 BF

[56] References Cited

U.S. PATENT DOCUMENTS 4,296,120 10/1981 Kadin .................................. 424/274

Primary Examiner—Robert Gerstl
Attorney, Agent, or Firm—George Iarnowski

[57] ABSTRACT

There are disclosed compounds of the formula

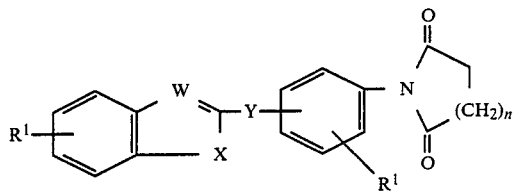

wherein
W is

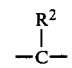

or $-N-$;

X is $-O-$, $-S-$,

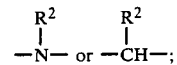

Y is $-CH_2O-$, $-OCH_2-$, $-CH_2S-$, $-SCH_2-$,

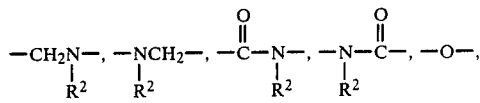

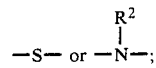

n is 0-3;
$R^1$ is hydrogen, loweralkyl, loweralkoxy or halo;
$R^2$ is hydrogen or loweralkyl;

and the pharmaceutically acceptable salts thereof, and their use in the treatment of leukotriene-mediated nasobronchial obstructive airpassageway conditions, such as allergic rhinitis, allergic bronchial asthma and the like.

3 Claims, No Drawings

NOVEL HETEROCYCLIC COMPOUNDS AS ANTIALLERGIC AGENTS

This invention relates to novel heterocyclic compounds possessing slow-reacting substance of anaphylaxis (SRS-A) antagonist activity which are useful as anti-inflammatory and antiallergic agents.

It is known that arachidonic acid (AA) is metabolized in mammals by two distinct pathways. The metabolism of arachidonic acid by cyclooxygenase enzymes results in the production of prostaglandins and thromboxanes. The physiological activity of these AA metabolites has been amply elucidated in recent years. The other pathway of AA metabolism involves lipoxygenase enzymes and results in the production of a number of oxidative products called leukotrienes. The latter are designated by the LT nomenclature system, and the most significant products of the lipoxygenase metabolic pathway are the sulfidopeptide leukotrienes $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J. Immun.* 215, 115–118 (1980); *Biochem. Biophsy. Res. Commun.* 93, 1121–1126 (1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature* 288, 484–486 (1980), and also S. E. Dahlen, *Acta Physiologica Scandinavica*, Supplement 512, (1983)], and another leukotriene, $LTB_4$, is a powerful chemotactic factor for leukocytes [see A. W. Ford-Hutchinson, *J. Roy. Soc. Med.*, 74, 831–833 (1981)]. The activity of leukotrienes and slow-reacting substances (SRS's) as mediators of inflammation and hypersensitivity is extensively reviewed in Bailey and Casey, *Ann. Reports Med. Chem.*, 17, 203–217 (1982).

The biological activity of the leukotrienes and SRS's indicates that a rational approach to drug therapy to prevent, remove or ameliorate the symptoms of allergies, anaphylaxis, asthma and inflammation must focus on antagonizing their effects. Thus, compounds which inhibit the biological effects of the leukotrienes and SRS's are considered to be of value in treating such conditions as allergic bronchial asthma, allergic rhinitis, as well as in other immediate hypersensitivity reactions.

The invention provides novel compounds of the formula

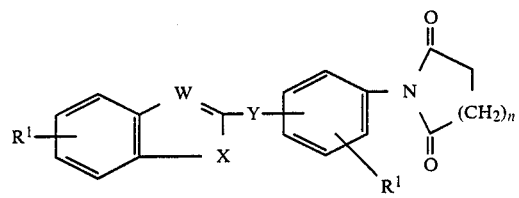

wherein

W is

or $-N-$;

X is $-O-$, $-S-$,

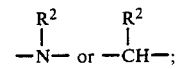

Y is $-CH_2O-$, $-OCH_2-$, $-CH_2S-$, $-SCH_2-$,

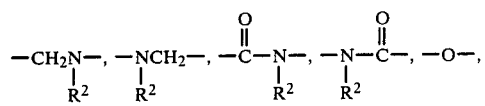

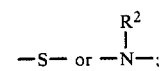

n is 0–3;

$R^1$ is hydrogen, loweralkyl, loweralkoxy or halo;

$R^2$ is hydrogen or loweralkyl;

and the pharmaceutically acceptable salts thereof.

The term "halo" refers to fluoro, chloro, and bromo. The terms "loweralkyl" and "loweralkoxy" refer to moieties having 1–6 carbon atoms in the carbon chain.

The compounds of the invention can be prepared in a number of ways. The basic compounds, with the moiety

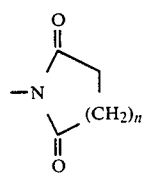

such as a 2,5-pyrrolidindione, can be prepared by the following reaction sequence in which Y is $-CH_2O-$:

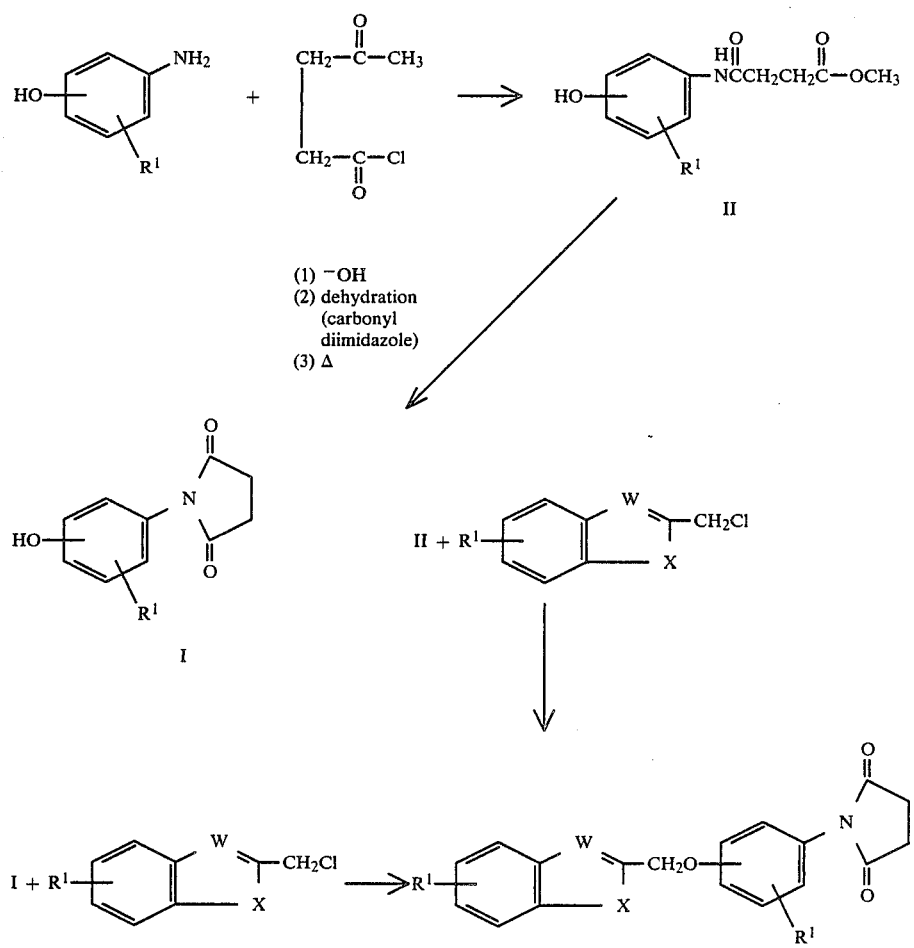

Compounds in which the bridge Y is —CH$_2$S— and —CH$_2$N— can be prepared in a like manner, using the appropriate aminothiophenol or aminoaniline in place of the aminophenol. Compounds in which the bridge Y is

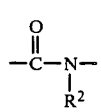

can be prepared by using the appropriate heterocyclic acyl chloride or acyl N-imidazole and the appropriate N-substituted aminoaniline.

The starting compounds for the preparation of compounds in which the linking bridge Y is —O—, —S— or

can be prepared by the following reaction sequence:

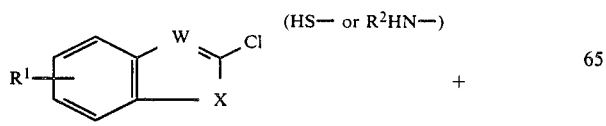

-continued

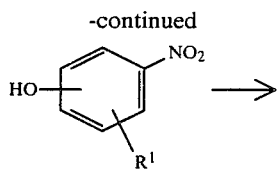

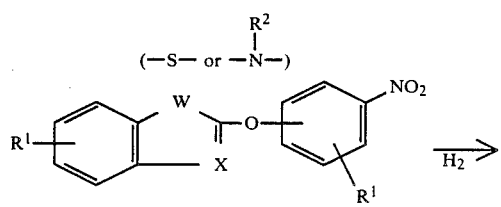

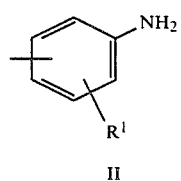

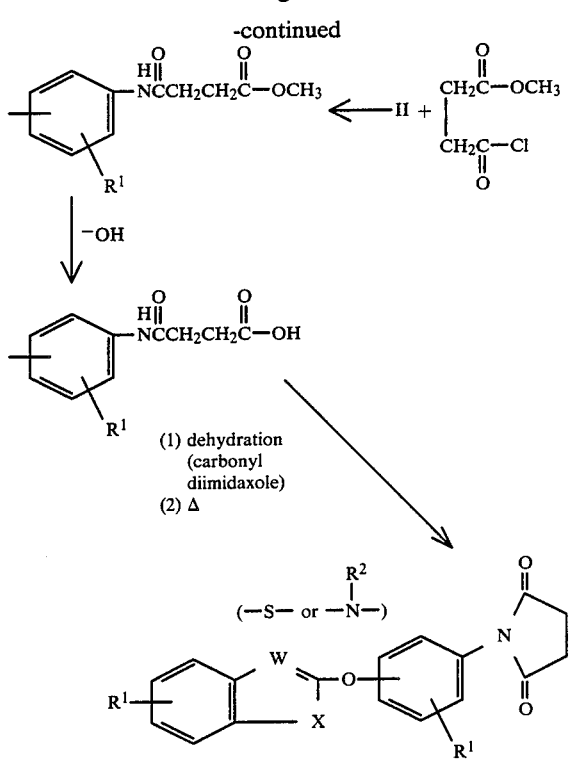

where the appropriate starting compounds are commercially available or can be conveniently prepared by conventional preparative techniques.

In all instances, the starting compounds used in the reaction sequences are either commercially available or can be readily prepared by conventional preparative methods readily apparent to those skilled in the art.

Compounds of the invention which contain a basic nitrogen are capable of forming pharmacologically acceptable salts, including the salts of pharmacologically acceptable organic and inorganic acids such as hydrochloric, hydrobromic, sulfuric, nitric, phosphoric, methanesulfonic, benzenesulfonic, acetic, citric, fumaric, maleic, succinic and the like. The compounds which are carboxylic acids or have a hydroxamic function are capable of forming alkali metal and alkaline earth carboxylates and carboxylates of pharmacologically acceptable cations derived from ammonia or a basic amine. Examples of the latter include but are not limited to cations such as ammonium, mono-, di-, and trimethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl-piperidinium, 2-methylpiperidinium, 1-ethyl-2-methylpiperidinium, mono-, di-, and triethanolammonium, ethyl diethanolammonium, n-butylmonoethanolammonium, tris(hydroxymethyl)methylammonium, phenylmonoethanolammonium, and the like.

The compounds of the invention, by virtue of their ability to antagonize the effects of $LTD_4$ and $LTC_4$, which are the major constituents of SRS-A, are useful for the inhibition of symptoms induced by these leukotrienes. Accordingly, the compounds are indicated in the prevention and treatment of those disease states in which $LTD_4$ and $LTC_4$ are causative factors, for example allergic rhinitis, allergic bronchial asthma and other leukotriene mediated naso-bronchial obstructive air-passageway conditions, as well as in other immediate hypersensitivity reactions, such as allergic conjunctivitis. The compounds are especially valuable in the prevention and treatment of allergic bronchial asthma.

When the compounds of the invention are employed in the treatment of allergic airways disorders, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The leukotriene antagonist effects of the compounds of the invention may be demonstrated by standard pharmacological procedures, which are described more fully in the examples given hereinafter.

The procedure described illustrates the ability of the compounds of the invention to antagonize $LTD_4$-induced bronchospasm mediated by exogenously administered leukotrienes.

The following examples show the preparation and pharmacological testing of compounds within the invention.

EXAMPLE 1

N-[3-[(2-benzothiazolyl)methoxy]phenyl]pyrrolidin-2,5-dione (A) 4-[[3-(hydroxy)phenyl]amino]-4-oxobutanoic acid, methyl ester To an ice cold solution of 3-aminophenol (21.8 g, 0.2 mol) and triethylamine (21.3 g, 0.2 mol) in tetrahydrofuran (250 ml) is added a solution of 3-carbomethoxypropanoyl chloride (30.1 g, 0.2 mol) in tetrahydrofuran. The reaction is allowed to warm to room temperature and is filtered through a pad of Celite and silica gel. The solvent is removed in vacuo to give a solid. Recrystallization from ethyl acetate gives 39.3 g (88% yield) of product, m.p. 144.5°–146° C.

(B) 2-chloromethylbenzothiazole

To a solution of aminothiophenol (8.3 g) in methylene chloride at 0° C. is added methyl chloroacetimidate hydrochloride[1] (8.6 g). The reaction is allowed to warm to room temperature while stirring overnight. The mixture is washed with water three times; dried over magnesium sulfate and concentrated to an oil. The oil is distilled (120°–135° C. at 0.5 mm Hg) to give 7.8 g (71% yield) of product.

[1]Prepared according to procedures described by R. Rogers and D. G. Nielson, Chem. Rev., 61, 179 (1961).

(C) N-[3-[(2-benzothiazolyl)methoxy]phenyl]pyrrolidin-2,5-dione

A mixture of 4-[[3-(hydroxy)phenyl]amino]-4-oxobutanoic acid, methyl ester (1.45 g, 6.5 mmol), 2-chloromethylbenzothiazole (1.20 g, 6.5 mmol), cesium carbonate (1.0 g), sodium carbonate (0.7 g), potassium iodide (5 mg) and acetone (60 ml) is heated at reflux for 2 hours. The reaction is filtered through a pad of Celite and silica gel and the solvent is removed in vacuo. Recrystallization from acetone gives 1.34 g (56% yield) of product, m.p. 175°–176° C.

Analysis for: $C_{18}H_{14}N_2O_3S$. Calculated: C, 63.89; H, 4.17; N, 8.27. Found: C, 63.50; H, 4.36; N, 8.19.

EXAMPLE 2

Following the procedure of Example 1 and using appropriate starting material and reagents, the following component is prepared: N-[3-[(1-methyl-2-benzimidazolyl)methoxy]phenyl]pyrrpolidin-2,5-dione, having a melting point of 150°–151.5° C.

Analysis for: $C_{19}H_{17}N_3O_3$. Calculated: C, 68.04; H, 5.10; N, 12.43. Found: C, 67.61; H, 5.19; N, 12.34.

EXAMPLE 3

The assay of this Example measures the in vivo ability of the components of the invention to inhibit the bronchospasm induced in guinea pigs by the exogenously administered leukotrienes $C_4$ and/or $D_4$. This assay is essentially a measure of the SRS-A antagonist properties of the compounds tested.

This assay is carried out as follows:

Male Hartley strain guinea pigs (350–600 g) are anesthetized with pentobarbital sodium (50 mg/kg, i.p.). The jugular vein is cannulated for injection of drugs and the carotid artery for monitoring blood pressure. The trachea is cannulated for artificial ventilation by a miniature Starling pump and for indirect measurement of respiratory volume changes as described infra. Additional pentobarbital sodium (15 mg/kg, i.v.) is administered to arrest spontaneous respiration. Submaximal bronchoconstrictor responses are established in control animals by varying the dose-levels of leukotriene. Intravenous dose-levels for $LTC_4$ range from 1 to 2 µg/kg and for $LTD_4$ the range is from 0.3 to 1 µg/kg. The aerosol bronchoprovocation dose for $LTC_4$ is generated from 1.6 µM solution and for $LTD_4$ from a 2.0 µM solution.

Test drugs are administered either intravenously, intraduodenally, by aerosol or orally at 1 or 10 minutes before induction of bronchospasm by administration of either $LTC_4$ or $LTD_4$ at the predetermined dose-levels. Aerosols of soluble drugs or leukotrienes are produced in-line for 10 seconds only by actuation of an ultrasonic nebulizer (Monaghan). Aerosolized drug dosage is expressed in terms of solution concentration and by a fixed aerosol exposure time (approximately 10 seconds). Control animals receive saline in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at 1, 3 and 5 minutes are obtained from the recorded charts.

The overflow volume at 1, 3 and 5 minutes is expressed as a percentage of maximal bronchoconstriction. Combined group values are used from each of these time intervals to determine the inhibitory effect of drugs.

$$\% \text{ inhibition} = \frac{\% \text{ bronchoconstriction (bc) in control group} - \% \text{ bc in drug-treated groups}}{\% \text{ bc in control group}} \times 100$$

Students t-test for unpaired data is used to determine statistical significance. Dose response curves are generated and $ED_{50}$ doses are interpolated from the regression lines.

Results for a compound of the invention in this assay, using $LTD_4$ for induction of bronchospasm, is given below:

TABLE II

| Compound of Example Number | Compound administered at 10 minutes before induction of bronchospasm | | |
|---|---|---|---|
| | Dose mg/kg (Intraduodenal) | % Inhibition Overflow Volume at | |
| | | 3 min. | 5 min. |
| 1 | 50 | 63 | 68 |
| 2 | 50 | 75 | 78 |

The results show that compounds of the invention show in vivo activity against $LTD_4$ induced bronchoconstriction.

What is claimed is:

1. A compound having the formula

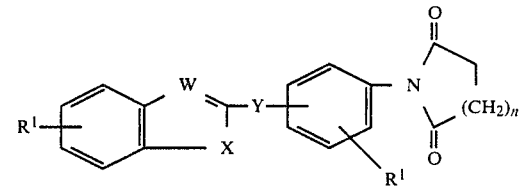

wherein
W is

or —N—;
X is —O—, —S—,

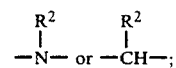

Y is —CH₂O—, —OCH₂—, —CH₂S—, —SCH₂—,

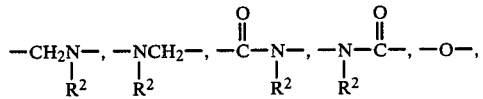
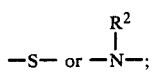
n is 0-3;
R[1] is hydrogen, loweralkyl, loweralkoxy or halo;
R[2] is hydrogen or loweralkyl;
and the pharmaceutically acceptable salts thereof.
2. The compound of claim 1, which is N-[3-[(2-benzothiazolyl)methoxy]-phenyl]pyrrolidin-2,5-dione.
3. The compound of claim 1, which is N-[3-[(1-methyl-2-benzimidazolyl)methoxy]phenyl]pyrrolidin-2,5-dione.
* * * * *